United States Patent [19]

Yates, Jr. et al.

[11] Patent Number: 4,877,584

[45] Date of Patent: Oct. 31, 1989

[54] TEMPERATURE PROGRAMMED SPECTROSCOPY TECHNIQUES

[76] Inventors: John T. Yates, Jr., 8602 Irvington Ave., Bethesda, Md. 20817; Gregory L. Griffin, Dept. of Chemical Engr. & Materials Science, University of Minnesota, Minneapolis, Minn. 55455; Maya Kiskinova, Institut fur Grenzflachenforschung und vakuum phusik, KFA.IGV, Postfach 1913, D-5170, Julich 1, Fed. Rep. of Germany

[21] Appl. No.: 41,594

[22] Filed: Apr. 22, 1987

Related U.S. Application Data

[62] Division of Ser. No. 416,666, Sep. 10, 1982, Pat. No. 4,663,297.

[51] Int. Cl.$^4$ .................. G01N 25/00; G01N 30/00
[52] U.S. Cl. .................................. 422/88; 73/863.11; 73/863.72; 73/863.73; 73/864.21; 73/864.81; 324/468; 422/94; 422/98
[58] Field of Search ............... 34/26; 55/20; 73/19, 73/863.11, 863.71, 863.72, 863.73, 864.21, 864.81; 250/281, 282, 288; 324/71.5, 468, 469; 374/14, 54; 422/88, 94, 95, 98; 436/5, 7, 37, 148, 147, 182, 183

[56] References Cited

U.S. PATENT DOCUMENTS

| | | | |
|---|---|---|---|
| 2,742,585 | 4/1956 | Zemany | 324/468 X |
| 3,610,023 | 10/1971 | Ageikin et al. | |
| 3,845,301 | 10/1974 | Wernlund et al. | 250/287 |
| 3,852,037 | 12/1974 | Kolb et al. | 422/54 |
| 4,025,605 | 5/1977 | Dalton, Jr. et al. | |
| 4,170,901 | 10/1979 | Conkle et al. | |
| 4,224,595 | 9/1980 | Dolan | 422/88 X |
| 4,305,724 | 12/1981 | Micko | 422/94 X |
| 4,327,054 | 4/1982 | Yasuda et al. | 73/27 R X |
| 4,399,684 | 8/1983 | Advani et al. | 73/1 G |

FOREIGN PATENT DOCUMENTS

| | | | |
|---|---|---|---|
| 494778 | 3/1976 | Australia | 324/71.5 |
| 55-83845 | 6/1980 | Japan | 422/94 |
| 2013901 | 8/1979 | United Kingdom | 422/94 |

OTHER PUBLICATIONS

Barrer, R. M., and Sutherland, J. W., *Proc. Roy. Soc. Ser.* A 237, 439 (1956).
Barrer, R. M., Bultitude, F. W., and Sutherland, J. W., *Trans. Faraday Soc.* 53, 111 (1957).
Redhead, P. A., *Vacuum* 12, 203 (1962).
Cvetanovic, R. J., and Amenomiya, Y., in "Advances in Catalysis and Related Subjects," vol. 17, p. 103, Academic Press, New York/London, 1967.
Bezus, A. G., Kiselev, A. V., Sedlacek, Z., and Du, P. Q., *J. Chem. Soc. Faraday Trans.* 67, 468 (1971).
King, D. A., Madey, T. E., and Yates, J. T., Jr., *J. Chem. Phys.* 55, 3236 (1971); 55, 3247 (1971).
Baranski, A., Ceckiewicz, S., and Caluszka, J., *Bull. Acad. Pol. Sci. Ser. Sci. Chim.* 24, 645 (1976).
Iwamoto, M., Maruyama, K., Yamazoe, N., and Seiyama, T., *J. Phys. Chem.* 81, 622 (1976).
Chan, Y. C., and Anderson, R. B., *J. Catal.* 50, 319 (1977).
Doelle, H. S., and Riekert, L., in "Molecular Sieves—II" (J. R. Katzer, Ed.), p. 401, ACS Symposium Series No. 40, Amer. Chem. Soc., Washington, D.C., 1977.

(List continued on next page.)

*Primary Examiner*—Barry S. Richman
*Assistant Examiner*—Timothy M. McMahon
*Attorney, Agent, or Firm*—Majestic, Parsons, Siebert & Hsue

[57] ABSTRACT

Temperature programmed spectroscopy wherein particles of a substrate under investigation are attached in a non-overlapping manner to a heating filament. The temperature of the filament is increased in a controlled manner, thus increasing the temperature of the attached substrate particles as well. An instrument for analyzing the gases is a mass spectrometer. Gases desorbed from the particles can be studied according to this technique, or the nature of heterogeneous catalytic chemical reactions of a gaseous atmosphere on the particles' surface may alternatively be detected and studied.

3 Claims, 2 Drawing Sheets

OTHER PUBLICATIONS

Rudham, R., and Stockwell, A., in "Catalysis—vol. 1" (specialist Periodic Reports), (D. A. Dowden, Ed.), p. 87, The Chemical Society, London, 1977.

Rabo, J. A., Bezman, R. D., and Poutsma, M. L., *Acta Phys. Chem.* 24, 39 (1978).

Harlfinger, R., Hoppach, D., Hofman, H. P., and Quitzsch, K., *Z. Phys. Chem. Leipzig* 260, 905 (1979).

Gorte, "Design Parameters for Temperature Programmed Desorption from Porous Catalysts", *Journal of Catalysis*, 75, pp. 164–174 (1982).

Yates, Jr., "The Thermal Desorption of Adsorbed Species," *Methods of Experimental Physics*, vol. 22, pp. 425–464 (1985).

Kishinova et al., "Thermal Desorption Spectroscopy from High–Specific–Area Solids . . . ", *Journal of Catalysis*, vol. 71, pp. 278–287, Oct. 1981.

Brenner et al., "Experimental Errors in the Application of Temperature-Programmed Desorption to Practical Catalysts", *Journal of Catalysis*, vol. 56, pp. 134–138 (1979).

Konvalinka et al., "Temperature Programmed Desorption of Hydrogen from Nickel Catalysts", *Applied Catalysis*, vol. 1, pp. 141–158 (1981).

PROGRAMMABLE POWER SUPPLY

TEMPERATURE PROGRAMMED SPECTROSCOPY TECHNIQUES

RIGHTS OF THE U.S. GOVERNMENT

The invention described herein may be manufactured and used by or for the Government of the United States without the payment of any royalties thereon or therefor.

CROSS-REFERENCE TO RELATED APPLICATIONS

This is a division of application Ser. No. 416,666, filed Sept. 10, 1982 now U.S. Pat. No. 4,663,297.

BACKGROUND OF THE INVENTION

This invention is related to the art of kinetic spectroscopy wherein gases either desorbed from or resulting from a catalytic reaction on a substrate surface are detected as a function of the temperature of the surface, generally referred to as temperature programmed desorption spectroscopy.

The art of thermal desorption spectroscopy is primarily directed to the study of substrate surfaces by analyzing the characteristics of desorption of controlled gaseous molecules from the surface. When a solid surface is exposed to gaseous molecular species, the species often form an adsorbed layer on the solid surface. The molecules adhere to the surface by either chemical or physical bonds. The high area substrate material is often in the form of small particles which are held in a bed of particles. The temperature of this bed is gradually increased in a vacuum or carrier gas environment. Gases desorbed from the surface area of these particles are analyzed by instruments such as a gas chromatograph or a mass spectrometer. The desired information output is the change in partial pressure in the desorbed gas as a function of the temperature of the bed of substrate particles. Peaks in differential partial pressure occur at different bed temperatures, providing information on the characteristics, including composition, of the substrate particle surface as it interacts with the adsorbed species under investigation.

There are certain recognized limitations of this technique. One such limitation is that diffusion through the bed of particles may interfere with measurements of desorption rates. That is, gas molecules desorbed from one particle may be adsorbed by another and then again desorbed before escaping the bed of particles and reaching the gas analyzer. Another difficulty is maintaining the temperature of all particles in the bed at the same temperature as the temperature is programmed upwards. The undesired result of these two factors is that the output data is blurred; that is, the desired sharp peaks of differential partial pressure do not appear but rather are blurred together.

The approach taken by existing technology is to extract the desired peak information from the blurred output data. This involves complicated computer implemented processing of that data. It is a principal object of the present invention to provide a technique for measuring the desired desorption peaks in a simpler and more accurate way.

It is a further object of the present invention to provide a system and general technique for all types of temperature programmed spectroscopy, including, in addition, the investigation of catalytic reaction chemistry, pore diffusion in porous substrate materials, and catalyst preparation using hydrogen or other gaseous reducing agents.

SUMMARY OF THE INVENTION

These and additional objects are accomplished by the various aspects of the present invention wherein, briefly, the substrate particles are spread out and held in a substantially non-overlapping manner over a surface whose temperature is raised in a controlled manner. A preferred surface is that of an electrically heated filament whose surface is inert. The temperature of all of the substrate particles supported by the filament is easily maintained uniform as the filament temperature is raised as a function of time. Diffusion of gases between particles is minimized and substantially eliminated by spreading the particles out, away from each other.

When using this arrangement for thermal desorption spectroscopic studies of the substrate particle surfaces, molecules of a gas of interest, previously adsorbed onto the surface of the substrate particles, are desorbed from those surfaces as the temperature of the electrical filament is raised by controllably increasing the electrical current through the filament. The desorption peaks as directly measured are sharp and no complicated processing of the measured data is necessary to extract the desired information from these peaks. The desorption measurement process is accomplished at a very low pressure within an appropriate chamber and the preferred gas detector is a very sensitive quadrupole mass spectrometer.

Other studies can also be accomplished by using the arrangement of substrate particles spread out over a controllably heated surface, according to another aspect of the invention. For example, catalytic reactions of gases with the substrate surfaces may be studied by introducing, into a chamber containing the substrate particles, reactant gases at around atmospheric pressure. Gaseous products of the reaction are removed from the chamber by a very small orifice and analyzed as a function of the filament temperature.

The applicants herein have published many details of their invention in an article appearing in the October, 1981 issue of *Journal of Catalysis*, Volume 71, pages 278–287. That paper is expressly incorporated herein by reference.

Additional objects, advantages and features of the various aspects of the present invention are included in the following description of their preferred embodiments, which description should be taken in conjunction with the accompanying drawings.

DESCRIPTION OF THE PREFERRED EMBODIMENTS

Figure 1:
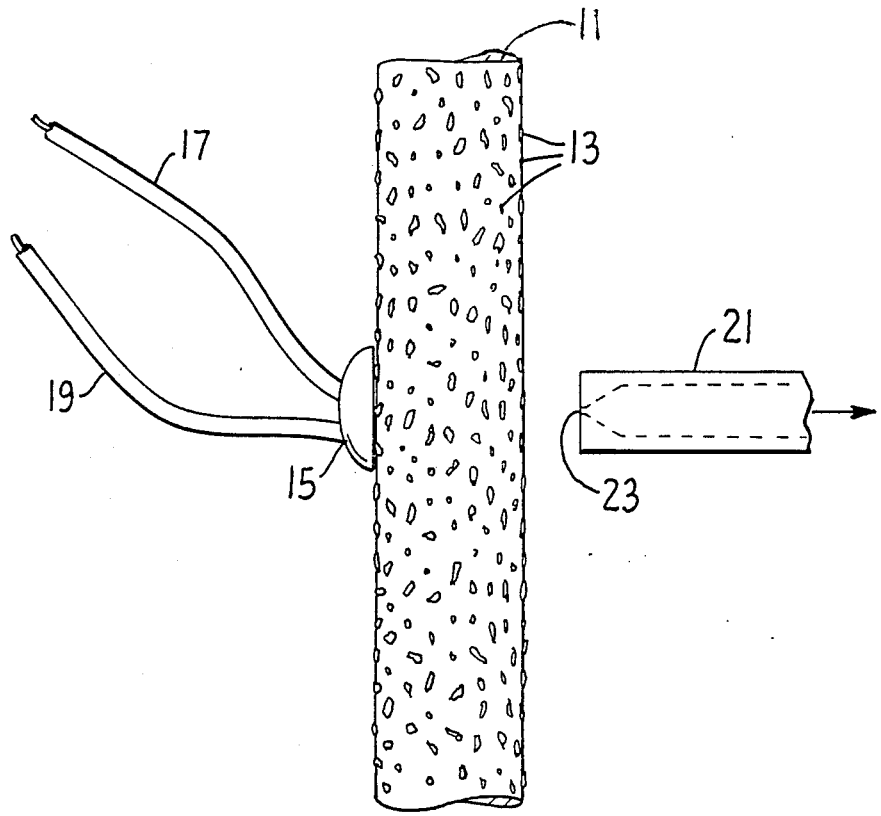
FIG. 1 is an enlarged view of a plurality of substrate particles attached to a heated surface.

Referring to FIG. 1, an electrical filament of circular cross-section is shown many times enlarged. A thermocouple 15 is welded to one point along the length of the filament 11, and carries information as to the temperature of that point over wires 17 and 19. Attached to the filament's surface near the thermocouple 15 are a large number of small particles 13 of a desired substrate material or materials to be investigated. A small tube 21 is positioned so that a tiny orifice 23 at its end is very close to the surface of the filament 11. Its purpose is to sample gases from a region adjacent to filament 11 for introduction to the mass spectrometer analyzer, as better shown in FIGS. 3 and 4, when catalytic reactions of the substrate are being studied in a gas phase environment. The sampling tube 21 can be of the form of a fine capillary tube or a small orifice of small enough size to sample gas at a rate appropriate for the mass spectrometer and the turbopump.

Figure 2:
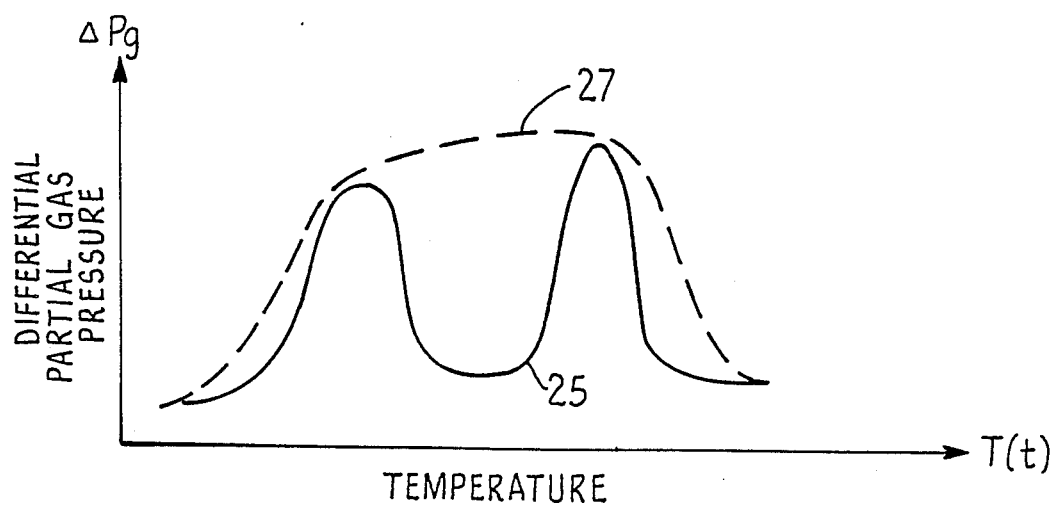
FIG. 2 is a schematic curve illustrating typical results desired from a temperature programmed spectrometer.

Referring to FIG. 2, a curve 25 is given for purposes of explanation to show two sharp peaks which gives information as to the nature and composition of the substrate particles 13. The curve 25 shows the differential partial pressure of gas being desorbed from the surfaces of the particles 13 in a vacuum as a function of the temperature of those particles. The temperature of the particles is gradually raised by increasing the electrical current through the filament 11 in a programmed manner. The two peaks of the curve 25 reveal that there are two different bonding modes for the adsorbed species on the substrate particles' 13 surface. The temperature at which the peaks occur are characteristic of these surface bonding modes. The area of the curve at a peak is proportional to the number of sites of that particular substrate material that hold a molecule of the gas that is analyzed. The gases that are desorbed by this gradual heating of the substrate particles 13 have previously been adsorbed by exposing the particles to the gas.

A blurred peak 27 is shown in dotted outline in FIG. 2 as illustrative of the type of information that is obtained according to present techniques of thermal desorption spectroscopy wherein the particles are held together in a bed or group. As described above, such a distribution of the particles may lead to intergranular diffusion of desorbed gas molecules and an uneven temperature of the substrate particles. This blurring of the data output is corrected, according to the present invention, by correcting the conditions that cause the blurring, rather than attempting to compensate for it by processing the blurred data 27 in order to identify the peaks 25, as is done by others using existing techniques.

The particles 13 can conveniently be attached to the surface of the filament 11 by depositing on a section of the filament a slurry mixture of the particles 13 in a solvent, followed by evaporation of the solvent. Once the filament 11 dries, the particles remain adhered to it. The surface of the filament 11 should be inert; that is, it should not itself give off gas molecules to any substantial degree which would interfere with detecting the gas molecules of particular interest. It has been found that a tungsten filament with its outer surface being lightly oxidized is satisfactory. If there is any substantial amount of undesired gas molecules emitted from the filament, a control filament without substrate particles attached to it can be included as part of any spectrometer in order to determine the component of the output readings due to the filament itself, which components can then be subtracted from the measurements made on the sample filament.

Figure 3:
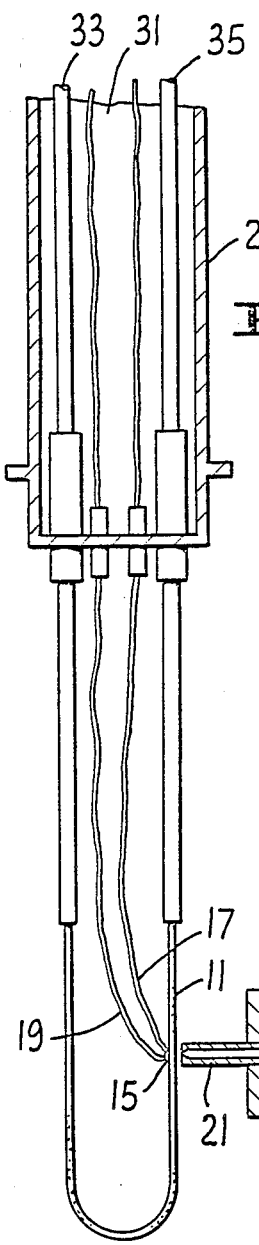
FIG. 3 shows a sub-assembly of such a spectrometer which utilizes the substrate particle holding technique according to FIG. 1.

Referring to FIG. 3, a sub-assembly of a temperature programmed spectrometer is illustrated which uses the system of FIG. 1. A container 29 of a cooling liquid 31 serves to support at its bottom the filament 11 in a loop. The temperature of the cooling liquid serves to define the lower limit of adsorption temperature for the sample. Wires 33 and 35 are connected to opposite ends of the filament 11. As is shown in FIG. 4, the filament energizing conductors 33 and 35 and the thermocouple conductors 17 and 19 are connected to a programmable power supply 37, which may be adjusted to program the filament temperature at various desired rates.

Figure 4:
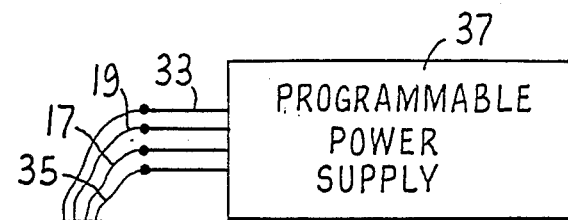
FIG. 4 shows in schematic form the essential elements of a complete spectrometer system which includes the sub-assembly of FIG. 3.
Figure 4:
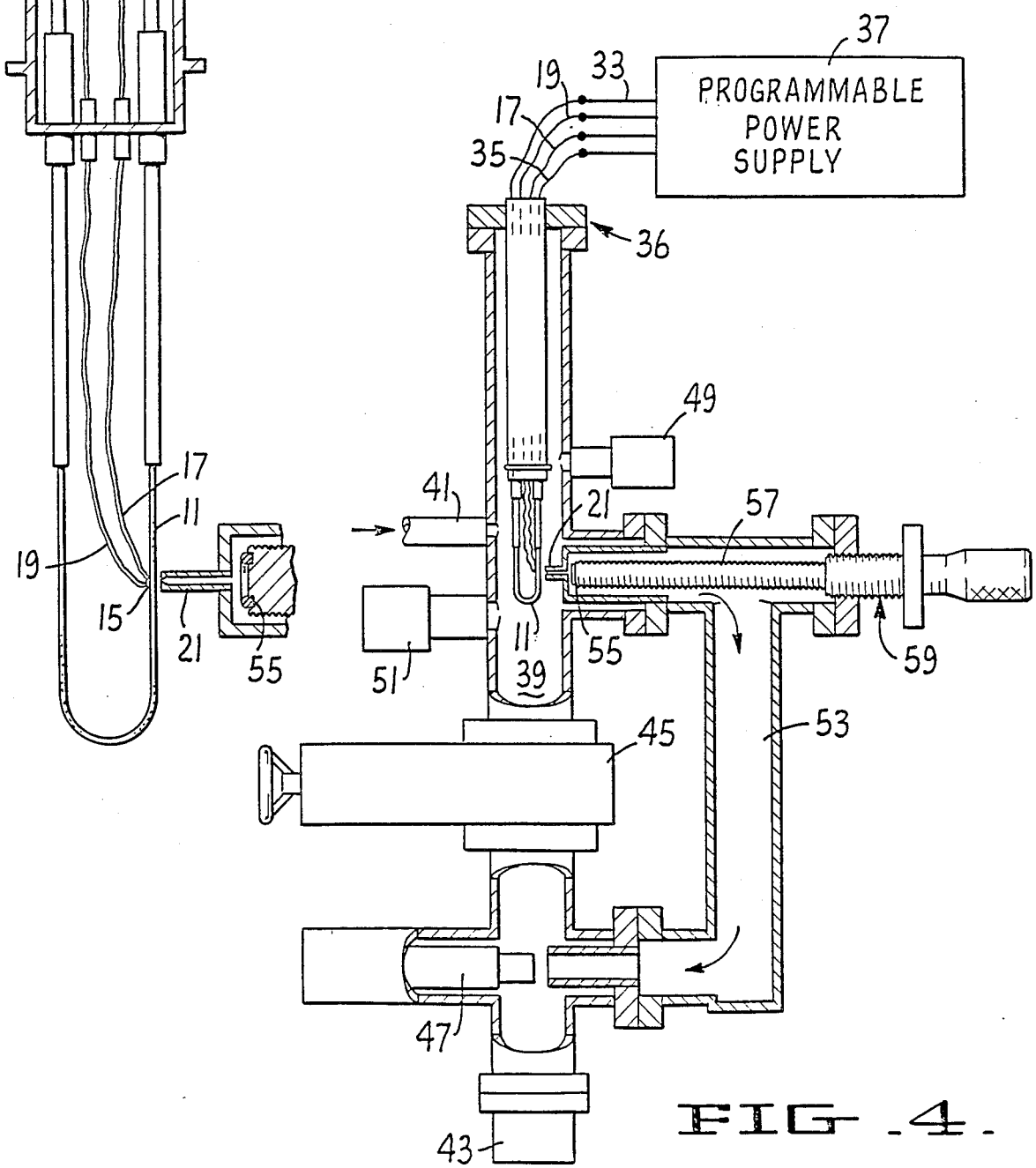

The sub-assembly of FIG. 3, as shown in FIG. 4, is contained within a vacuum chamber 39. The filament sub-assembly may be conveniently removed by opening the support flange assembly 36. The temperature of the filament 11 is raised in a predetermined manner by a programmed electrical current increase through the filament.

The apparatus of FIG. 4 is capable of being used to study either the desorption of gases from the particles or the catalytic reaction of the particle surfaces with the gases, as discussed previously. In either case, a gas inlet tube 41 is provided into the enclosed chamber 39. Gases are admitted into the chamber through the tube 41. When the system of FIG. 4 is being used for desorption spectroscopy, the single gas of interest is first introduced into the chamber so that the particles previously attached to the filament can adsorb the gas on its surfaces. The chamber 39 is then evacuated by the use of a turbopump 43 through a gate valve 45 which is held open during this process. Once the chamber 39 is evacuated, the filament 11 is gradually increased in temperature and gases desorbed from the substrate surfaces are measured by a quadrupole mass spectrometer 47 through the gate valve 45 which is held open. This provides the information previously discussed with respect to FIG. 2 concerning the substrate surface characteristics. Since typical base pressures prior to desorption are very low (less than $1 \times 10^{-8}$ torr), the sensitivity of the mass spectrometer detector is enhanced, permitting very small substrate samples to be employed. The low base pressure is achieved by using materials of construction in the apparatus which have low outgassing rates. The high mass spectrometer sensitivity gives large output signals with a small amount of gas present, and the high vacuum condition of the instrument of FIG. 4 results in an extremely low undesired background signal.

Certain other measuring instruments are connected with the chamber 39. A capacitance manometer 49 is connected to the chamber 39 through an appropriate port. Similarly, a Bayard Alpert gauge 51 is connected through another port to the chamber 39. Also, for many applications, it is desirable to have a transparent window portion in a wall of the chamber 39 so that the geometrical conditions within the chamber can be observed from the outside.

The capillary needle 21 is not utilized when the system of FIG. 4 is used for desorption spectroscopy but when the system is used for high pressure catalytic reaction chemistry with the surfaces of particles attached to the filament 11, gases drawn through the small tube 21 become the source for the mass spectrometer 47 and are applied thereto through a wide bore tabulation 53. A copper focusing insert is provided in the passage 53 on the same axis as mass spectrometer 47 in order to better focus the available gases into the mass spectrometer 47. This increases the efficiency and sensitivity of the instrument. A capillary 21 is opened and closed by a valve formed of an O-ring seal 55 at the end of a linear translation element 57. The element 57 is moved back and forth by a micrometer control assembly 59 of a conventional design. When the linear translation element 57 is pulled away from the small tube 21, its capillary opening then communicates with the mass spectrometer 47 through the passage 53. This passage is closed off by moving the element 57 so that the seal 55 presses tightly against the surface surrounding the small tube 21. By valving the capillary opening through the tube 21 at this position, there is a very small dead-space volume within that tube and within the O-ring seal that retains gases after it is closed off. A small dead-space volume is desired in order to provide a fast response to the detection of different gases from the reactor chamber 39 at subsequent times. The volume can be reduced even further by a single ball-like resilient element in the center of the end of the longitudinal translator element 57 to replace the O-ring 55 and close off the inner end of the tube 21 directly.

When operating the system of FIG. 4 in its second mode to study the catalytic reaction of gases with substrate particles, the chamber 39 is first evacuated by the turbopump 43 with the gate valve 45 opened. The valve 45 is then closed. Desired gases are introduced into the chamber 39 through the inlet 41 until the desired composition and pressure within the chamber 39 is reached. The filament 11 is then increased in temperature in a programmed manner and the mass spectrometer 47 receives gases through the small tube 21 for analysis without significantly reducing the pressure in the chamber 39. In addition, the system may be operated as a static catalytic reactor by maintaining the filament at a constant temperature sufficient to produce a measurable rate for the catalytic reaction.

It will be recognized that the system of FIG. 4 and the techniques described above can be used in a wide range of chemical processes at the surface of high specific area solids. Among them is the study of adsorption/desorption processes, the investigation of catalytic reaction chemistry, the investigation of pore diffusion in zeolites and other porous materials, and the investigation of catalyst preparation using hydrogen or other gaseous reducing agents.

Although the various aspects of the present invention have been described with respect to its preferred embodiments, it will be understood that the invention is entitled to protection within the full scope of the appended claims.

It is claimed:

1. Apparatus for analyzing gaseous reactions on a surface of a quantity of material, comprising:
   an enclosed reaction chamber,
   means connectable to said chamber for introducing gas thereinto,
   means connectable to said chamber for controlling pressure of the gas therein,
   an electrically resistive filament held within said chamber and adapted to carry a quantity of material thereon,
   means connecting an electrical potential across said filament for controlling the level of electrical current therethrough, whereby heating of said filament and any material carried thereon may be controlled,
   means including a tube extending from outside said chamber and terminating within said chamber at one end in an orifice positioned adjacent to but spaced apart from said filament for extracting gas from a region of said chamber adjacent said filament,
   means attached to an area of said filament surface in the vicinity of said tube end orifice for providing an electrical signal that is proportional to temperature of said surface area, whereby the temperature of the surface of a quantity of material carried by said filament adjacent said area may be monitored, and
   means continuously receiving gas from said gas extracting means at another end of said tube outside of said chamber for analyzing the gas removed from the region adjacent said filament, whereby the product of any gaseous reactions on the surface of the quantity of material carried by said filament in said region may be analyzed.

2. Apparatus according to claim 1 wherein said gas analyzing means includes a mass spectrometer.

3. Apparatus according to claim 1 which additionally comprises means supporting said filament within said chamber for cooling electrical conductors to said filament from outside of said chamber, whereby the temperature of the filament within said chamber can be controlled.

* * * * *